United States Patent [19]

Fischell et al.

[11] Patent Number: 5,605,530
[45] Date of Patent: Feb. 25, 1997

[54] SYSTEM FOR SAFE IMPLANTATION OF RADIOISOTOPE STENTS

[76] Inventors: Robert E. Fischell, 14600 Viburnum Dr., Dayton, Md. 21036; Tim A. Fischell, 1018 Chancery La., Nashville, Tenn. 37215; David R. Fischell, 71 Riverlawn Dr., Fair Haven, N.J. 07704

[21] Appl. No.: 408,780

[22] Filed: Mar. 23, 1995

[51] Int. Cl.$^6$ ..................................................... A61N 5/00
[52] U.S. Cl. ...................................................... 600/3
[58] Field of Search .................... 600/1–8; 606/7

[56] References Cited

U.S. PATENT DOCUMENTS

| 5,120,973 | 6/1992 | Rohe et al. | 600/7 |
| 5,199,939 | 4/1993 | Dake et al. | 600/8 |
| 5,213,561 | 5/1993 | Weinstein et al. | 600/7 |

FOREIGN PATENT DOCUMENTS

| 0254351 | 1/1988 | European Pat. Off. | 600/7 |
| 0649412 | 3/1979 | U.S.S.R. | 600/7 |
| 9304735 | 3/1993 | WIPO | 600/7 |

OTHER PUBLICATIONS

Hopkins et al, "A Remote Reservoir Injection Accessory for Reducing Exposure" Mar. 1981.

*Primary Examiner*—Angela D. Sykes
*Assistant Examiner*—John P. Lacyk
*Attorney, Agent, or Firm*—Morton J. Rosenberg; David I. Klein

[57] ABSTRACT

There is provided a radiation shield for protecting a health care worker from ionizing radiation prior to and during delivery of a radioisotope stent into a patient's blood vessel. The radiation shield is placed coaxially over at least a distal portion of a stent delivery catheter assembly carrying or having formed therein a radioactive stent. The radiation shield is maintained about the distal portion of the catheter assembly until delivery of the radioactive stent is to occur. During the stent's delivery, the catheter assembly is axially displaced relative to the radiation shield to pass therethrough, then into the patient's blood vessel. A protective barrier is thus continually maintained between the health care worker and the radioactive stent he or she is delivering.

14 Claims, 6 Drawing Sheets

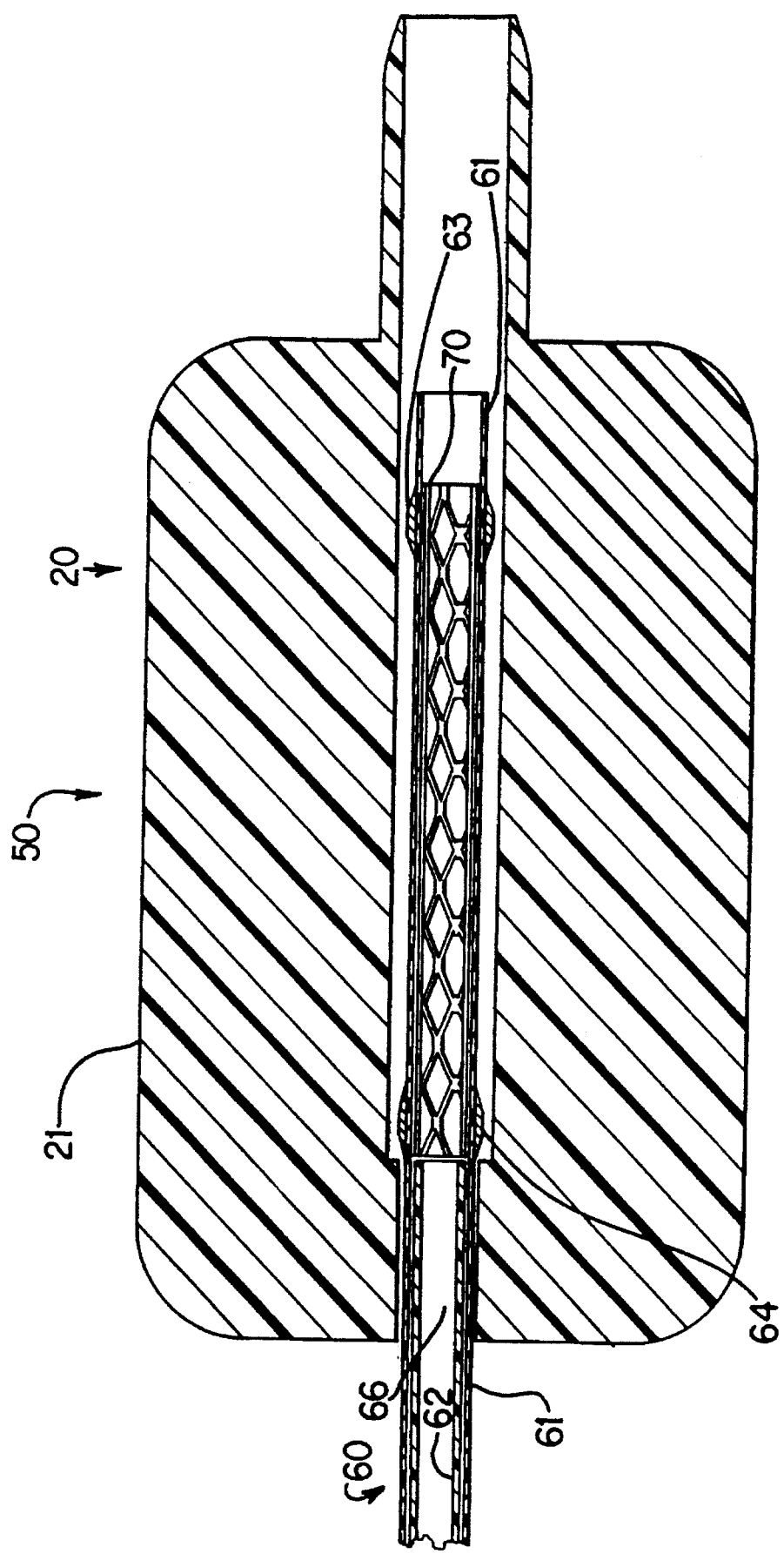

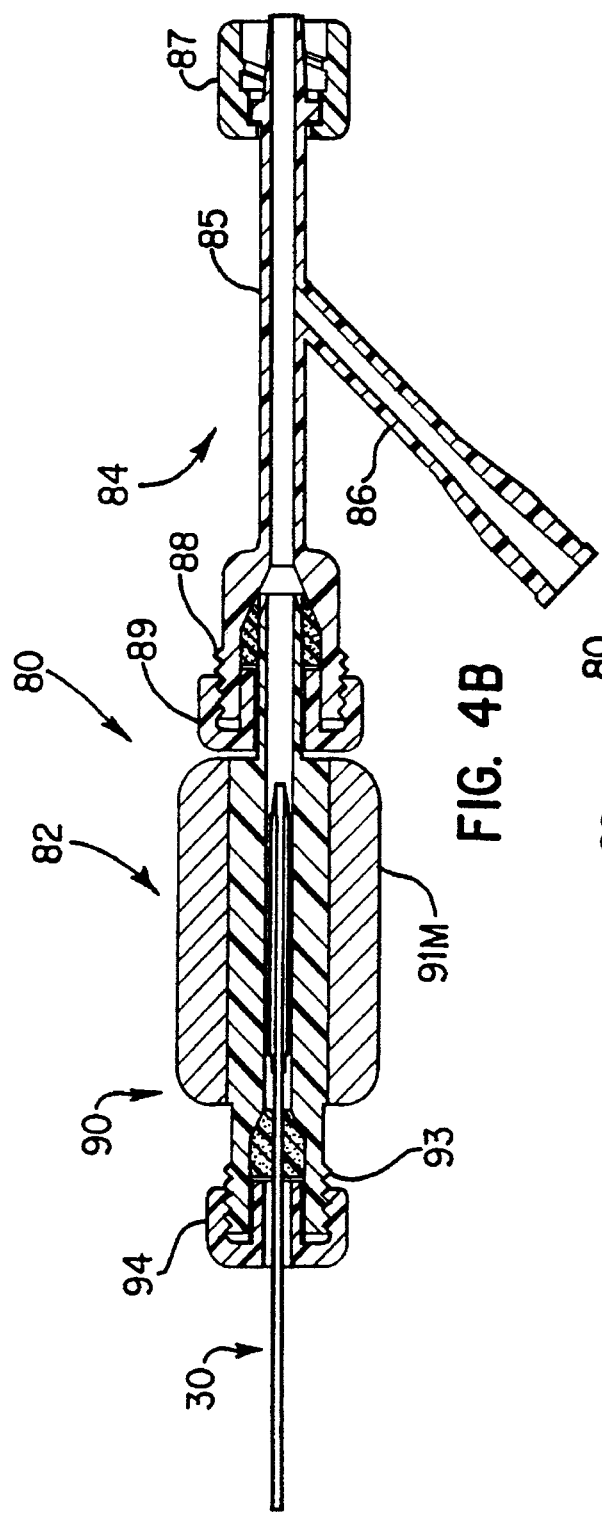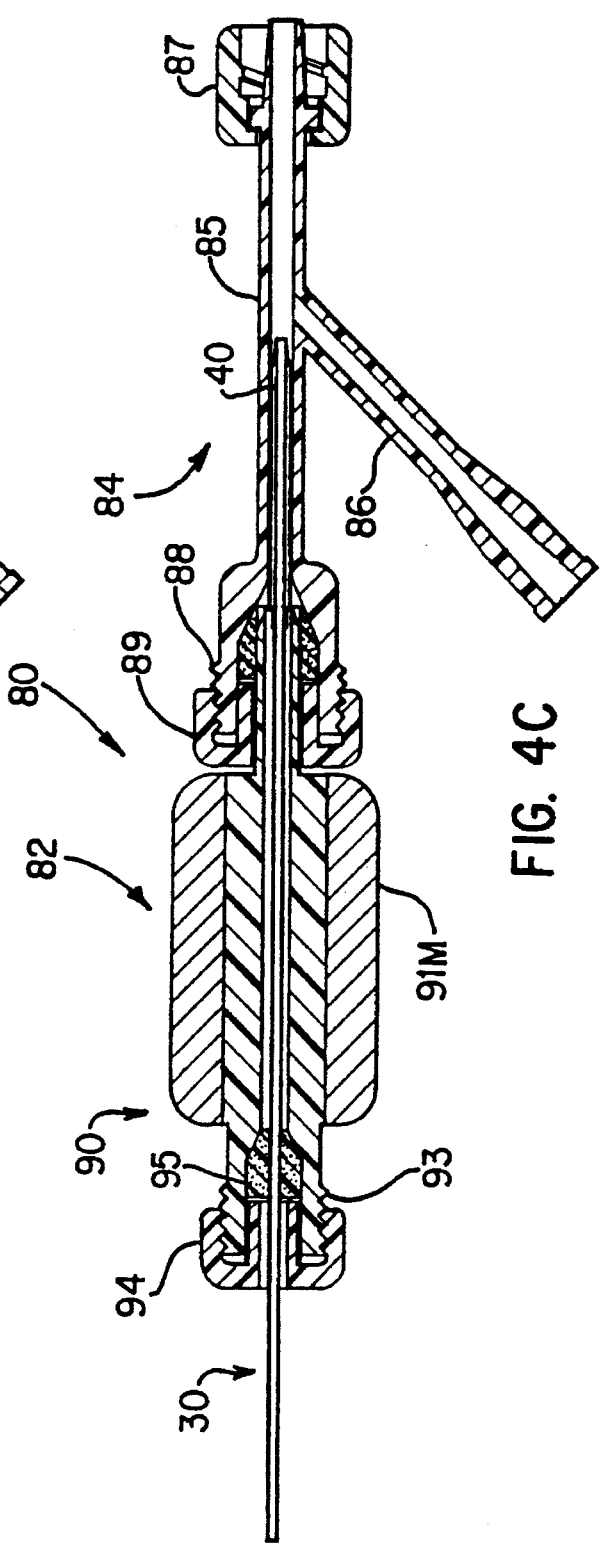

SYSTEM FOR SAFE IMPLANTATION OF RADIOISOTOPE STENTS

FIELD OF USE

This invention is in the field of devices to protect health care workers from being exposed to ionizing radiation while inserting radioisotope stents into a vessel of the human body.

BACKGROUND OF THE INVENTION

U.S. Pat. Nos. 5,059,166 and 5,176,617 describe radioisotope stents that can be used to mechanically maintain patency of a human vessel while simultaneously preventing the growth of proliferating tissue. However, there is no prior art that describes how to protect health care workers from being exposed to ionizing radiation when inserting such stents into a vessel of the human body.

SUMMARY OF THE INVENTION

The present invention includes a radiation shield that is placed over a radioisotope stent that is situated at a distal portion of a stent delivery catheter. The shield has a distal section having a smaller outside diameter as compared to most of the length of the generally cylindrical shield. This distal section is designed for insertion into the proximal end of a "Y" adaptor. When the nut of the Tuohy-Borst fitting of the "Y" adaptor is tightened down, the shield distal portion is frictionally joined to the "Y" adaptor. With the "Y" adaptor joined to a guiding catheter which is typically placed into the femoral artery at the groin, the shield becomes rigidly attached to the guiding catheter. The stent delivery catheter can then be used to deliver the radioisotope stent through the shield, through the "Y" adaptor and finally through the guiding catheter for insertion (for instance) into a coronary artery. When used in this manner, the interventional physician who is implanting the stent will not be exposed to any significant level of radiation from the radioisotope stent. Similarly, the shield could be inserted into the hemostasis valve of an introducer sheath for cases where a guiding catheter is not used.

Another embodiment of the radiation shield includes means that releasably join the shield to the stent delivery catheter by frictional forces. Specifically, the shield can include a type of Tuohy-Borst fitting at its proximal end which locks the shield to the stent delivery catheter when that the nut on the shield's Tuohy-Borst fitting is tightened down, but allows free motion of the stent delivery catheter through the shield when the nut is loosened.

Still another embodiment of this invention is a radiation shield used with a high intensity radiation source in the form of either a temporary stent or a wire-like catheter having a high intensity radiation source located at a distal portion of the catheter.

Thus it is an object of this invention to prevent heath care workers from being exposed to ionizing radiation when implanting either a permanent or a temporary radioisotope stent into a vessel of a human body.

Another object of this invention is to provide a radiation shield which can be fixedly joined to a "Y" adaptor which in turn is fixedly joined to a guiding catheter.

Still another object of this invention is that the shield can allow sliding motion of a radioisotope stent and stent delivery catheter through its central lumen.

Still another object of this invention is to be able to releasably attach the shield to a stent delivery catheter so that the shield does not inadvertently fall off the stent delivery catheter which would allow exposure of the health care workers to radiation.

Still another object of this invention is to be able to shield a distal portion of a wire-like catheter at which distal portion a high intensity radioisotope source is located.

These and other objects and advantages of this invention will become apparent to a person of ordinary skill in this art upon careful reading of the detailed description of this invention including the drawings as presented herein.

BRIEF DESCRIPTION OF THE DRAWINGS

FIG. 3 is longitudinal cross section of a radiation shield surrounding a self-expanding radioisotope stent that is placed within a distal portion of a stent delivery catheter.

FIG. 4B longitudinal cross section showing the distal section of the radiation shield being placed within the Tuohy-Borst fitting of the "Y" adaptor.

FIG. 4C is longitudinal cross section showing the radiation shield joined to the "Y" adaptor with the radioisotope stent and stent delivery catheter advanced through the shield and through the "Y" adaptor.

DETAILED DESCRIPTION OF THE DRAWINGS

Figure 1:
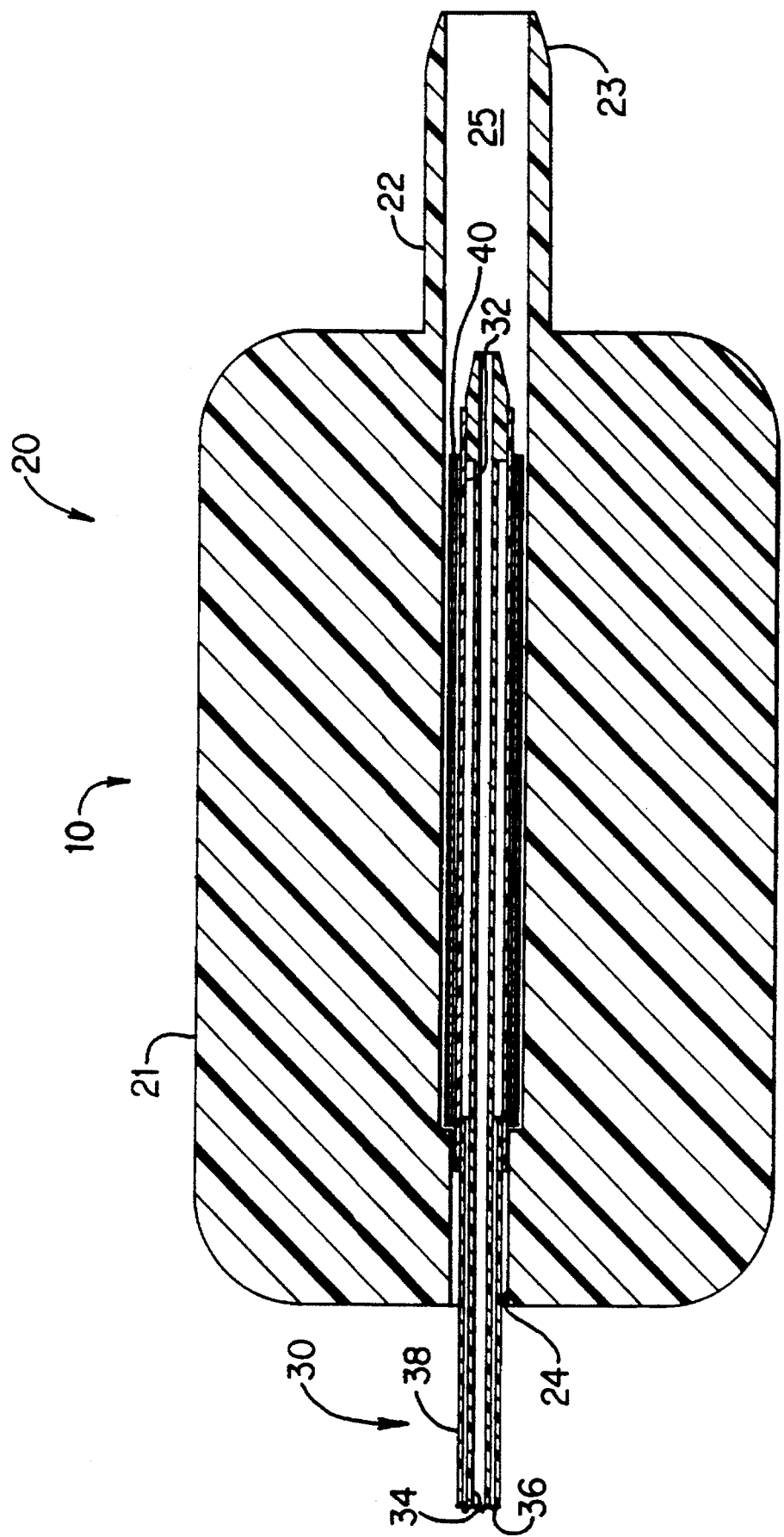
FIG. 1 is a longitudinal cross section of a radiation shield enclosing a balloon expandable radioisotope stent that is mounted on a distal portion of a balloon angioplasty catheter.

FIG. 1 illustrates a system 10 for preventing exposure of health care workers to radiation during delivery of a radioisotope stent 40 into a vessel of the human body. The system 10 includes a generally cylindrical radiation shield 20, a balloon angioplasty catheter 30 and a balloon expandable radioisotope stent 40 mounted onto the balloon 32 located at a distal portion of the catheter 30. The shield 20 has a generally cylindrical main body 21 and a generally cylindrical distal section 22 having a tapered distal end 23. It should be understood, however, that the shield could be used with a blunt distal end without the distal section 22. The shield's proximal lumen 24 can have a slightly smaller diameter as compared to the shield's distal lumen 25. This construction can prevent the radioisotope stent 40 (which is fixedly attached to balloon angioplasty catheter 30) from moving backward in a proximal direction. The inside diameter of the lumen 25 is just large enough to allow the stent 40 attached to the catheter 30 to be slideably advanced through the shield 20. The balloon angioplasty catheter 30 has a balloon 32 mounted onto an inner shaft 34 and an outer shaft 38. The annular passageway 36 is used for fluid to inflate the balloon, and the central lumen 34 forms a passageway for a guide wire (not shown).

Figure 2:
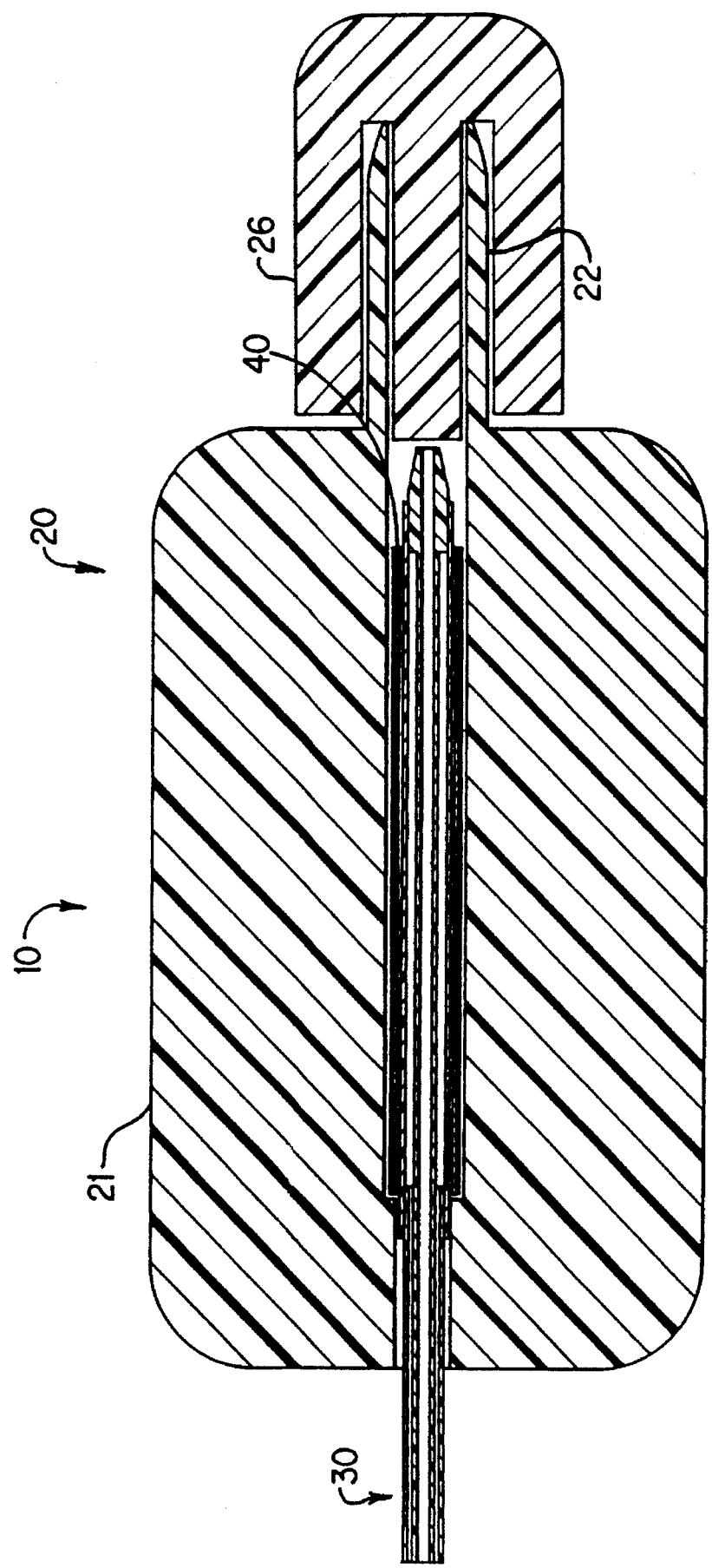
FIG. 2 is a longitudinal cross section of a radiation shield enclosing a balloon expandable radioisotope stent with a distal plug joined to a distal section of the radiation shield.

FIG. 2 shows the system 10 including the shield 20 and catheter 30 with a forward motion stop 26 frictionally attached to the distal section 22 of the shield 20. This design prevents the shield 20 from sliding off the catheter 30 and radioisotope stent 40 in either a forward or backward direction.

FIG. 3 illustrates a system 50 for delivering a self-expanding radioisotope stent into a vessel of the human body. The system 50 includes a radiation shield 20, a stent delivery catheter 60 and a self-expanding radioisotope stent 70. The stent delivery catheter 60 includes an outer sheath 61, a pusher tube 62, radiopaque marker bands 63 and 64, and a central lumen 66 through which a balloon catheter and/or a guide wire can be passed. This type of stent delivery catheter 60 is described in detail in U.S. patent application Ser. No. 08/351,498 which Application is included herein by reference.

Figure 4A:
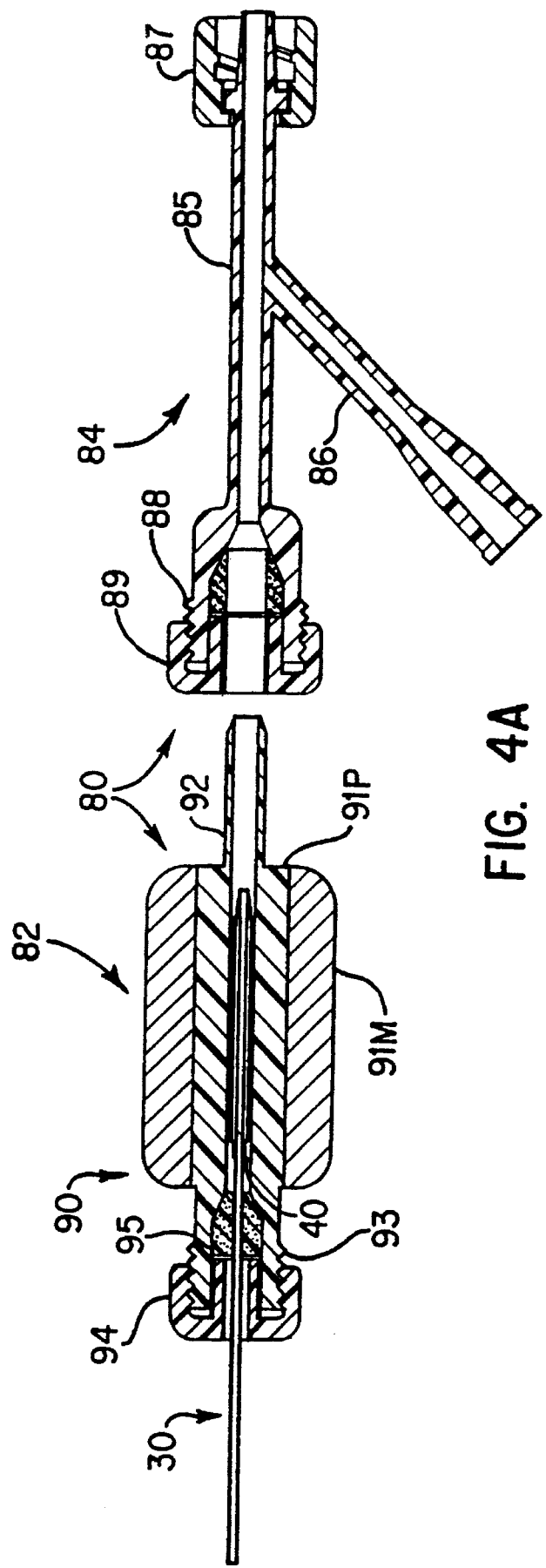
FIG. 4A illustrates a longitudinal cross section of a second embodiment of the radiation shield and a "Y" adaptor with these two devices being separated from each other.

FIGS. 4A, 4B and 4C illustrate an alternative embodiment system 80 for safely inserting a radioisotope stent into a vessel of the human body. The system 80 consists of a shield-stent-catheter subsystem 82, and a "Y" adaptor subsystem 84. The subsystem 82 consists of a radiation shield 90, a stent delivery (balloon angioplasty) catheter 30 and a balloon expandable radioisotope stent 40. The shield 90 consists of a main plastic body section 91P, a metal main body section 91M, a distal section 92 and a proximal, threaded section 93 onto which a nut 94 can be screwed. FIGS. 4A and 4B show the nut 94 tightened down onto the threaded section 93 so as to squeeze the deformable gland 95 thereby frictionally attaching the shield 90 to the catheter 30. Therefore, this proximal portion of the shield 90 operates as a typical Tuohy-Borst fitting. When the nut 94 is tightened down, the shield will not inadvertently slide off the catheter 30. Thus, a health care worker using the system 80 will be protected from accidental exposure to the radiation emanating from the radioisotope stent 40.

The system 80 would typically be used as follows:

(1) A sterile package containing the subsystem 82 would be opened with the nut 94 tightened down so as to frictionally join the shield 90 to the stent delivery catheter 30.

(2) The "Y" adaptor subsystem 84 would be joined by means of its distal Luer lock connector 87 to the proximal end of a guiding catheter (not shown) that has been placed into a vessel (typically the femoral artery) of a human body. The side arm 86 of the "Y" adaptor 84 would typically be connected to a manifold (not shown) for the delivery of contrast medium and/or medications.

(3) As shown in FIG. 4B, the distal section 92 of the shield 90 would be inserted into the Tuohy-Borst fitting 88 of the "Y" adaptor 84, and the nut portion 89 of the Tuohy-Borst fitting 88 would be tightened down so as to frictionally join the shield 90 to the "Y" adaptor 84.

(4) As shown in FIG. 4C, the nut 94 of the shield 90 would be loosened, and the assembly of the stent delivery catheter 30 and radioisotope stent 40 would be advanced through the main body 85 of the "Y" adaptor 84.

(5) After the radioisotope stent 40 is delivered at its appropriate site within the body, the stent delivery catheter 30 is completely removed from the shield 90, the nut 89 is then loosened, and the shield 90 is pulled out of the "Y" adaptor 84.

The shields 20 or 90 would most advantageously be molded from a clear, rigid plastic such as an acrylic or a polycarbonate. If a pure beta particle emitting isotope such as phosphorous 32 is used to make the stents 40 or 70 radioactive, then the diameter of the shield would typically lie between 1 and 3 cm with 2 cm being close to optimum. The length of the main body shield would typically be 1 to 2 cm longer than the length of the radioisotope stent 40 or 70. It is also envisioned that the shield could include a high density metallic section (as shown in FIGS. 4A, 4B and 4C), particularly if the radioisotope stent had a gamma radiation component.

Figure 5:
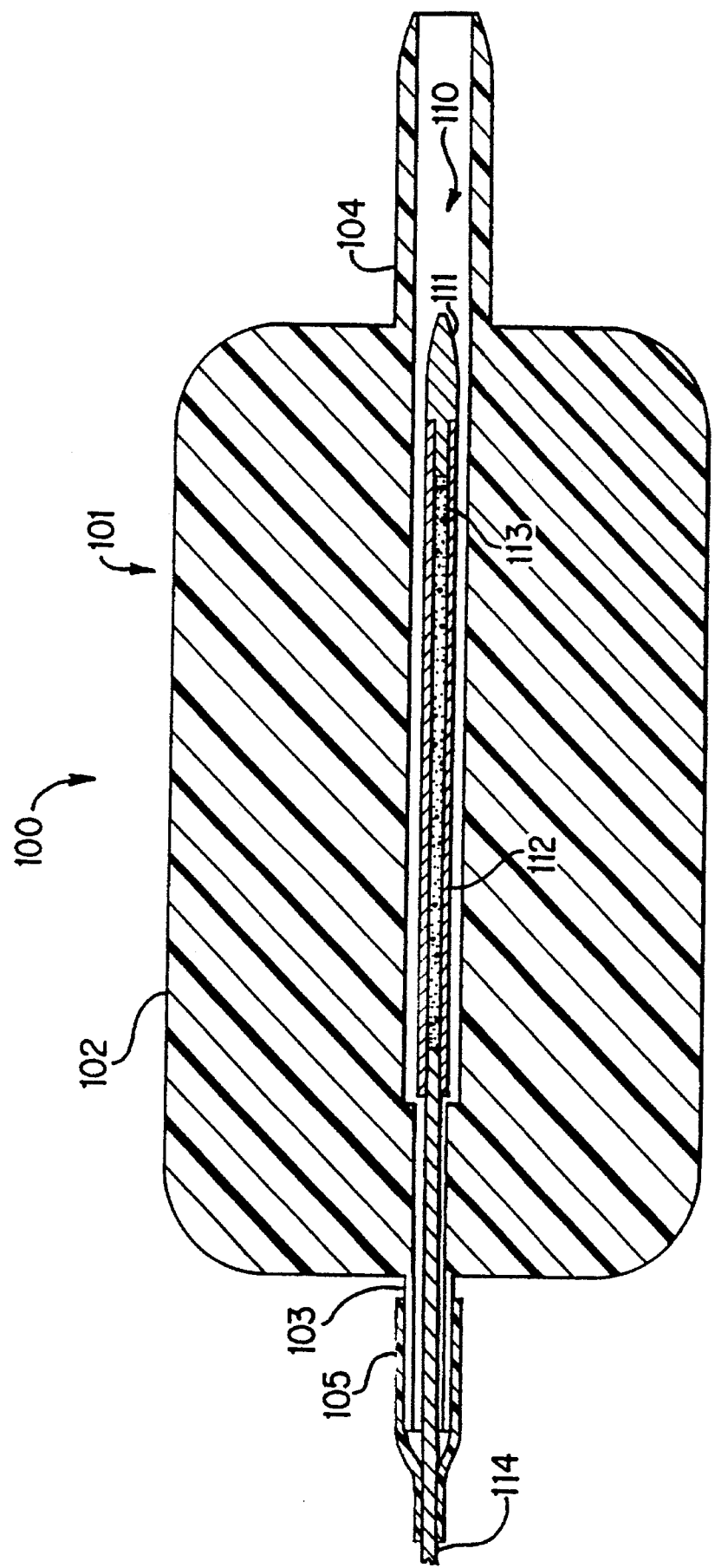
FIG. 5 is a longitudinal cross section of a radiation shield placed over a high intensity radioisotope source located at a distal portion of a wire-like catheter.

FIG. 5 illustrates a system 100 consisting of a radiation shield 101 and a radioactive tipped catheter 110. The radiation shield 101 has a generally cylindrical main body 102, a small diameter proximal section 103 and a small diameter distal section 104. The catheter 110 has a tapered distal tip 111, a thin-walled cylinder 112 containing a radioisotope 113, and an elongated wire 114. A pressure sensitive adhesive tape 105 can be used to attach the shield 101 to the catheter 110. When the tape 105 is removed, the catheter 110 can be slideably advanced through the shield 101 and into a vessel of a human body. The radioisotope 113 could be a high intensity (greater than 1.0 milliCurie) beta particle emitter such as phosphorous 32 or a beta and gamma emitter such as iridium 192. The cylinder 112 could be welded at its distal end to the tip 111 and welded at its proximal end to the wire 114 thus providing a hermetically sealed enclosure for the radioisotope 113. The cylinder 113 could be fabricated from a shape memory alloy such as Nitinol to form a temporary stent in the shape of a helical spring at some appropriate site within a vessel of a human body, or the cylinder 112 might retain a generally straight shape within the vessel. In either case, the system 100 would be used in a manner as previously described for systems 10, 50 and 80 to prevent health care workers using the system 100 from being exposed to ionizing radiation.

Various other modifications, adaptations, and alternative designs are of course possible in light of the above teachings. Therefore, it should be understood at this time that within the scope of the appended claims, the invention may be practiced otherwise than as specifically described herein.

What is claimed:

1. A system for preventing health care workers from being exposed to ionizing radiation when delivering a radioisotope stent into a vessel of a human body, the system comprising:

an axially extending stent delivery catheter assembly having a distal portion;

a radioisotope stent that is placed at the distal portion of the stent delivery catheter assembly; and, a radiation shield coaxially disposed externally about the distal portion of the stent delivery catheter assembly to shield health care workers using the system from exposure to ionizing radiation during insertion of the radioisotope stent into a vessel of the human body, the stent delivery catheter assembly being axially displaceable relative to the radiation shield, the radiation shield being maintained external to the vessel of the human body.

2. The system of claim 1 wherein the radiation shield includes a distal section which is smaller in diameter as compared to most of the length of the radiation shield.

3. The system of claim 2 further comprising a "Y" adaptor having a proximal end for receiving the distal section of the radiation shield, the proximal end having formed thereon threadedly adjusted securing means for releasably securing therein the distal section of the radiation shield.

4. The system of claim 1 further comprising a releasable attachment means located on the radiation shield for releasably attaching the radiation shield to the stent delivery catheter assembly.

5. The system of claim 4 wherein the releasable attachment means includes adjustment means threadedly coupled thereto for adjusting the attachment of the radiation shield to the stent delivery catheter assembly.

6. The system of claim 4 wherein the releasable attachment is in the general form of a pressure sensitive adhesive tape.

7. The system of claim 1 wherein the radiation shield is formed from a plastic material.

8. The system of claim 7 wherein the radiation shield is formed from a transparent plastic material.

9. The system of claim 8 wherein the plastic material is an acrylic.

10. The system of claim 8 wherein the plastic material is a polycarbonate.

11. The system of claim 1 wherein at least a first portion of the radiation shield is formed from a plastic material and at least a second portion of the radiation shield is formed from a metal.

12. The system of claim 1 wherein the radiation shield is formed entirely from a metal.

13. A system for preventing health care workers from being exposed to ionizing radiation when delivering a temporary radioisotope stent into a vessel of a human body, the system comprising:

an axially extending catheter assembly having a distal portion forming the temporary radioisotope stent adapted to be placed into a vessel of a human body; and a radiation shield coaxially disposed externally about the temporary radioisotope stent for shielding health care workers using the system from exposure to ionizing radiation during insertion of the temporary radioisotope stent catheter assembly into a vessel of a human body, the catheter assembly being axially displaceable relative to the radiation shield, the radiation shield being maintained external to the vessel of the human body.

14. A system for preventing health care workers from being exposed to ionizing radiation when delivering a high intensity radioisotope source into a vessel of a human body, the system comprising:

an axially extending catheter assembly having a distal portion forming the high intensity radioisotope source having an approximate intensity of at least one milli-Curie; and a radiation shield coaxially disposed externally about the high intensity radioisotope source for shielding health care workers using the system from exposure to ionizing radiation during insertion of the high intensity radioisotope source catheter assembly into a vessel of a human body, the catheter assembly being axially displaceable relative to the radiation shield, the radiation shield being maintained external to the vessel of the human body.

* * * * *